United States Patent
Chen et al.

(10) Patent No.: US 12,270,070 B2
(45) Date of Patent: Apr. 8, 2025

(54) SINGLE STRANDED CIRCULAR DNA LIBRARIES FOR CIRCULAR CONSENSUS SEQUENCING

(71) Applicant: Roche Sequencing Solutions, Inc., Pleasanton, CA (US)

(72) Inventors: Rui Chen, Fremont, CA (US); Toumy Guettouche, Pleasanton, CA (US); Aaron Richardson, Palo Alto, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 671 days.

(21) Appl. No.: 17/448,248

(22) Filed: Sep. 21, 2021

(65) Prior Publication Data

US 2022/0002787 A1    Jan. 6, 2022

Related U.S. Application Data

(60) Division of application No. 16/444,092, filed on Jun. 18, 2019, now Pat. No. 11,155,855, which is a continuation of application No. PCT/EP2017/083115, filed on Dec. 15, 2017.

(60) Provisional application No. 62/436,819, filed on Dec. 20, 2016.

(51) Int. Cl.
| | | |
|---|---|---|
| *C12Q 1/6811* | (2018.01) | |
| *C12Q 1/6806* | (2018.01) | |
| *C12Q 1/6834* | (2018.01) | |
| *C12Q 1/6855* | (2018.01) | |
| *C12Q 1/6876* | (2018.01) | |

(52) U.S. Cl.
CPC .......... *C12Q 1/6811* (2013.01); *C12Q 1/6806* (2013.01); *C12Q 1/6834* (2013.01); *C12Q 1/6855* (2013.01); *C12Q 1/6876* (2013.01)

(58) Field of Classification Search
None
See application file for complete search history.

(56) References Cited

U.S. PATENT DOCUMENTS

| | | |
|---|---|---|
| 6,692,915 B1 | 2/2004 | Nallur |
| 2002/0012930 A1 | 1/2002 | Rothberg et al. |
| 2004/0185484 A1 | 9/2004 | Costa et al. |
| 2014/0134610 A1 | 5/2014 | Pham et al. |

FOREIGN PATENT DOCUMENTS

| | | |
|---|---|---|
| WO | 2014/196863 A1 | 12/2014 |
| WO | 2015/188192 A2 | 12/2015 |

OTHER PUBLICATIONS

Vijay J. Gadkar and Martin Filion, "A novel method to perform genomic walks using a combination of single stranded DNA circularization and rolling circle amplificationt," Journal of Microbiological Methods 87:38-43 (2011).
Mark T. Gregory, et al., "Targeted single molecule mutation detection with massively parallel sequencing," Nucleic Acid Research 44(3):e22 (2016).
International Searching Authority, International Preliminary Report on Patentability for International Patent Application No. PCT/EP2017/083115 (Jun. 25, 2019).
International Searching Authority, International Search Report for International Patent Application No. PCT/EP2017/083115 (Jun. 28, 2018).
International Searching Authority, Written Opinion of the International Searching Authority for International Patent Application No. PCT/EP2017/083115 (Jun. 28, 2018).

*Primary Examiner* — Samuel C Woolwine
*Assistant Examiner* — Carolyn L Greene
(74) *Attorney, Agent, or Firm* — Eric Grant Lee

(57) ABSTRACT

The invention is a novel method of generating a library of circular single stranded nucleic acid molecules by utilizing circular capture molecules. The method is not limited by size of target nucleic acid molecules and can potentially accommodate very long molecules. The method finds application in nucleic acid sequencing, e.g., nanopore sequencing where unlimited-length templates can be read.

4 Claims, 1 Drawing Sheet

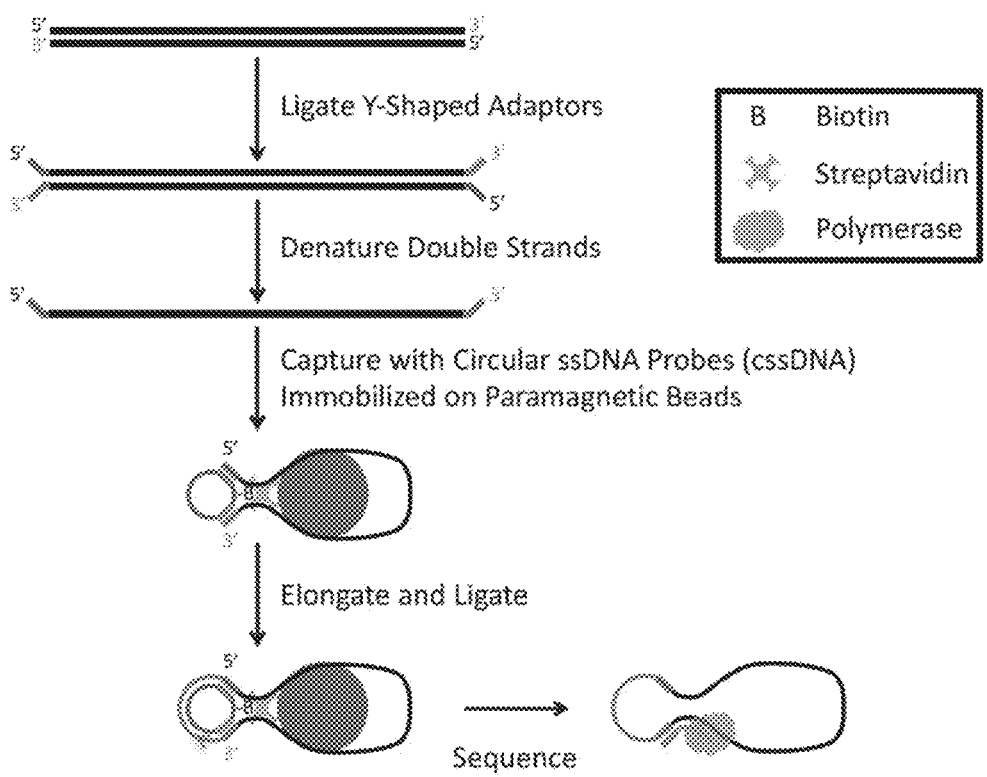

SINGLE STRANDED CIRCULAR DNA LIBRARIES FOR CIRCULAR CONSENSUS SEQUENCING

CROSS-REFERENCE TO RELATED APPLICATIONS

This patent application is a divisional patent application of U.S. patent application Ser. No. 16/444,092, filed Jun. 18, 2019, which is a continuation of International Patent Application No. PCT/EP2017/083115, filed Dec. 15, 2017, which claims priority to and the benefit of U.S. Provisional Patent Application No. 62/436,819, filed Dec. 20, 2016. Each of the above patent applications is incorporated herein by reference as if set forth in its entirety.

FIELD OF THE INVENTION

The invention relates to the field of nucleic acid sequencing. More specifically, the invention relates to the field of creating libraries of circular template DNA for single molecule sequencing.

BACKGROUND OF THE INVENTION

The current generation of nucleic acid sequencing methods utilizes libraries of target molecules from which each individual molecule is sequenced. Each molecule in the library comprises a target sequence to be analyzed conjugated to artificial sequences ("adaptors") necessary for the chosen sequencing method and sequencing instrument. Single molecule sequencing is often performed on double stranded DNA (dsDNA) molecules that have the same adaptor on both sides. Typically, sequencing these molecules yields data from both sense and anti-sense strand of each molecule in one read. In order to create sequencing libraries from only one strand, circularization of the target molecule with an adaptor or splint can be used. However, existing methods of generating circular single stranded libraries are inefficient and limited by the size of original target molecules. The method described herein is able to efficiently generate libraries of single stranded circular nucleic acid molecules regardless of the original molecule size.

SUMMARY OF THE INVENTION

In some embodiments, the invention is a method of making a library of circular single stranded target nucleic acid molecules from a sample comprising a plurality of double-stranded target nucleic acid molecules, the method comprising: ligating an adaptor to each end of the double-stranded target molecule, thereby forming an adaptor-ligated double-stranded molecule; denaturing the adaptor-ligated double-stranded molecule, thereby forming two strands of the adaptor-ligated molecule; annealing a capture molecule to each strand of the adaptor-ligated molecule, wherein the capture molecule is a circular single-stranded nucleic acid molecule comprising two sequences complementary to at least a portion of the adaptor, thereby forming a hybrid molecule comprising the capture molecule hybridized to the adaptor sequences at the 5'-end and the 3'-end of the strand of the adaptor-ligated molecule; extending the 3'-end of the strand of adaptor-ligated molecule to reach the 5'-end of the strand of adaptor-ligated molecule; ligating the 5'-end and the 3'-end of the strand of adaptor-ligated molecule, thereby forming a hybrid molecule comprising the capture molecule and a circularized strand of adaptor-ligated molecule; and separating the capture molecule from the circularized strand of adaptor-ligated molecule, thereby forming a library of circular single stranded target nucleic acid molecules.

In some embodiments, the adaptor comprises at least one double-stranded region and at least one single-stranded region, each comprising two strands. In some embodiments the adaptor comprises at least one barcode and at least one primer binding site. In some embodiments, the capture molecule comprises two sequences complementary to at least a portion of the single-stranded region of the adaptor. In some embodiments, the capture molecule comprises two sequences complementary to the single-stranded region and the double stranded region of the adaptor. In some embodiments the barcode is a multiplex sample identifying barcode (MID) or a unique molecular identifying barcode (UID). In some embodiments the primer is a sequencing primer. In some embodiments the sequences complementary to at least a portion of the adaptor are located diametrically opposite one another in the capture molecule.

In some embodiments the capture molecule comprises one or more or all of a barcode, a primer binding site and a binding moiety for being captured by a solid support. In some embodiments, the capture molecule is biotinylated. In some embodiments, the capture molecule is immobilized on the solid support such as a streptavidin-coated bead or surface during binding to the target molecule.

In some embodiments, the invention is a method of sequencing target nucleic acids in a sample comprising a plurality of target molecules, the method comprising: creating a library of circular target nucleic acid molecules from the sample using the method described above, wherein the adaptors further comprise a binding site for a sequencing primer; annealing the sequencing primer to the binding site; and extending the sequencing primer, thereby obtaining the sequence of the target nucleic acid. In some embodiments, the sequencing primer is extended by a DNA polymerase such as Phi 29 polymerase. In some embodiments the sequence is obtained by measuring the incorporation of labeled nucleotides during primer extension. In some embodiments, the sequence is obtained by a nanopore-based method.

In some embodiments, the invention is an alternative method of making a library of circular single stranded target nucleic acid molecules from a sample comprising a plurality of double-stranded target nucleic acid molecules, the method comprising: ligating an adaptor to each end of the double-stranded target molecule, thereby forming an adaptor-ligated double-stranded molecule; denaturing the adaptor-ligated double-stranded molecule, thereby forming two strands of the adaptor-ligated molecule; annealing a capture molecule to each strand of the adaptor-ligated molecule, wherein the capture molecule is a different circular single-stranded nucleic acid molecule comprising two adjacent sequences complementary to at least a portion of the adaptor, thereby forming a hybrid molecule comprising the capture molecule hybridized to the adaptor sequences at the 5'-end and the 3'-end of the strand of the adaptor-ligated molecule; ligating the 5'-end and the 3'-end of the strand of the adaptor-ligated molecule hybridized to adjacent sequences on the capture molecule, thereby forming a hybrid molecule comprising the capture molecule and a circularized strand of the adaptor-ligated molecule; separating the capture molecule from the circularized strand of the adaptor-ligated molecule, thereby forming a library of circular single stranded target nucleic acid molecules.

In some embodiments, the invention is an alternative method of making a library of circular single stranded target nucleic acid molecules from a sample comprising a plurality of double-stranded target nucleic acid molecules, the method comprising: denaturing the double-stranded molecule, thereby forming two strands of the target molecule; annealing a capture molecule to each strand of the target molecule, wherein the capture molecule is a circular single-stranded nucleic acid molecule comprising two sequences complementary to at least a portion of the target molecule, thereby forming a hybrid molecule comprising the capture molecule hybridized to the sequences at the 5'-end and the 3'-end of the strand of the target molecule; extending the 3'-end of the strand of the target molecule to reach the 5'-end of the strand of the target molecule; ligating the 5'-end and the 3'-end of the strand of the target molecule, thereby forming a hybrid molecule comprising the capture molecule and a circularized strand of the target molecule; separating the capture molecule from the circularized strand of the target molecule, thereby forming a library of circular single stranded target nucleic acid molecules.

In some embodiments, the invention is a library of target nucleic acid molecule created using the method described above.

BRIEF DESCRIPTION OF THE DRAWINGS

FIG. 1 is a diagram of the method of generating a library of circular single stranded nucleic acid molecules according to the invention.

DETAILED DESCRIPTION OF THE INVENTION

Definitions

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual patient or from a model organism, including the formalin-fixed paraffin embedded tissues (FF-PET) and nucleic acids isolated therefrom. A sample may also include cell-free material, such as cell-free blood fraction that contains cell-free DNA (cfDNA) or circulating tumor DNA (ctDNA).

A term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) Helv. Chim. Acta 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. An oligonucleotide may be comprised of at least 6 nucleotides or about 15-30 nucleotides. Oligonucleotides are prepared by any suitable method known in the art, for example, by a method involving direct chemical synthesis as described in Narang et al. (1979) Meth. Enzymol. 68:90-99; Brown et al. (1979) Meth. Enzymol. 68:109-151; Beaucage et al. (1981) Tetrahedron Lett. 22:1859-1862; Matteucci et al. (1981) J. Am. Chem. Soc. 103:3185-3191.

The term "primer" refers to a single-stranded oligonucleotide which hybridizes with a sequence in a target nucleic acid ("primer binding site") and is capable of acting as a point of initiation of synthesis along a complementary strand of nucleic acid under conditions suitable for such synthesis. The primer binding site can be unique to each target or can be added to all targets ("universal priming site" or "universal primer binding site").

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion. An adaptor may contain sequences such as barcodes and universal primer or probe sites.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 10 nucleotides, so that in a sample, the nucleic acids incorporating the barcodes can be distinguished or grouped according to the barcodes.

The terms "multiplex identifier" and "MID" refer to a barcode that identifies a source of a target nucleic acids (e.g., a sample from which the nucleic acid is derived, which is needed when nucleic acids from multiple samples are combined). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The terms "unique molecular identifier" and "UID" refer to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" or "universal priming site" refer to a primer and primer binding site present in (typically, in vitro added to) different target nucleic acids. For example, the universal priming site may be included in an adaptor ligated to the plurality of target nucleic acids. The universal priming site may also be a part of target-specific (non-universal) primers, for example by being added to the 5'-end of a target-specific primer. The universal primer can bind to and direct primer extension from the universal priming site.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "sequencing" refers to any method of determining the sequence of nucleotides in the target nucleic acid.

Single molecule sequencing is often performed on double stranded DNA (dsDNA) molecules that have the same adaptor on both sides, here called symmetrically adapted sequencing template. Typically, sequencing these molecules yields data from at least a part of the sense and anti-sense strands in one sequencing read. (See U.S. Pat. No. 8,822, 150). In other technologies, the template is a topologically circular single stranded molecule containing two complementary strands linked together (See U.S. Pat. No. 9,404, 146). In order to create sequencing libraries from only one strand, circularization of the target molecule using an adaptor (See U.S. Provisional Application "Barcoded circular library construction for identification of chimeric products" Ser. No. 62/415,245 filed on Oct. 31, 2016) or splint (See U.S. Application Pub. No. 20120003657) can be used. However, this procedure is size limited due to CIRCLIGASE™ restrictions (up to 500 bp) in the former case or inefficient in the latter case. The method described herein allows the separation of the sense and anti-sense strands in two sequencing template molecules and is not limited by the size of the original double-stranded target molecule.

In one embodiment, the invention is a method of generating a library of single-stranded circular nucleic acids for sequencing. FIG. 1 depicts an example of the method of according to the invention.

In the first step, a plurality of double stranded DNA molecules is provided. The double stranded DNA molecules may be isolated genomic DNA or genomic DNA of reduced complexity (e.g., amplified selected regions of the genome or captured selected regions of the genome such as exome).

In the next step, the double stranded DNA molecules are ligated to adaptors on each end. The adaptor may comprise at least one ligatable double-stranded portion and at least one single stranded portion. In the example in FIG. 1, it is a Y-shaped adaptor. The non-complementary region may assume any configuration, e.g., a fork structure (Y-adaptors) or a stem-loop structure. The non-complementary region may contain one or two strands. The two strands may be of the same or different lengths. The non-complementary regions do not form stable hybrids at the reaction conditions and remain single stranded during the steps of the method of the invention. The adaptor may contain more than one double stranded region and more than one single stranded region. For example, a single-stranded region may be flanked by two double-stranded regions.

The double stranded target nucleic acid must comprise ends suitable for ligation of a double stranded adaptor. In some embodiments, the ends of the target nucleic acids are "polished," i.e., extended with a nucleic acid polymerase to ensure double-stranded ends. In some embodiments, the 5'-ends of the target nucleic acids are phosphorylated. In some embodiments, the ligation is a blunt-end ligation. In some embodiments, the ligation is a cohesive end ligation. The 3'-ends of the target nucleic acid are extended with a single nucleotide (e.g., A) and the adaptor is engineered to contain a complementary overhang (e.g., T) at the 3'-ends.

In the next step, the adaptor-ligated target DNA molecules are denatured and contacted with single stranded capture DNA circles (sscDNA molecules). Creation of small single-stranded DNA circles containing desired sequences is routine in the art and such circles are commercially available (Bio-Synthesis, Inc., Lewisville, Tex.). In the present invention, the circles have regions of complementarity to each of the two non-complementary sequences in the adaptors (FIG. 1). In some embodiments, the regions of complementarity can be separated by a desired distance. As will be seen from the following steps of the method, the sequence between the regions of complementarity is to be copied into the library molecules and thus may be used to incorporate additional sequences into the library molecules. In some embodiments, the additional sequences are selected from primer binding sites, restriction enzyme sites, barcodes, etc.

In some embodiments, the sscDNA molecules can be attached to a solid support. In some embodiments, the attachment to the solid support is via a biotin-streptavidin linkage effected by a biotin-labeled sscDNA molecule. In some embodiments, the solid support is a bead present in solution. In some embodiments, the bead is a polystyrene bead, a paramagnetic bead, an adsorbing bead, or a charged bead. In other embodiments, the solid support is a surface, e.g., a slide or an array. In the example in FIG. 1, the circular single-stranded nucleic acids molecule comprises a capturable moiety, e.g., is conjugated to biotin. The hybridization complex between the circular single-stranded nucleic acids molecule and the single stranded molecule with an adaptor sequence at each end can be captured, e.g., using streptavidin conjugated to a solid support such as a polymer bead.

The ratio of sscDNAs and denatured target molecules can be optimized for annealing of a single sscDNA to each strand of the adaptor-ligated target DNA molecule. Because the sscDNA molecule has two complementary sequences for each single strand of the target molecule, the spatial proximity will facilitate the binding of the second end of the target molecule to form the structure shown on FIG. 1. Binding of the sscDNA molecule and a strand of the target DNA molecule creates a structure with a free extendable 3'-end.

In the next step, the extendable 3'-end of the target DNA strand annealed to the sscDNA is extended with a DNA polymerase going around the sscDNA molecule to reach the 5'-end of the target DNA strand. In some embodiments, the DNA polymerase is a non-strand displacing polymerase. In some embodiments, the polymerase may be selected from a Taq, Klenow, Bst, Pfu, T4, T7, *E. coli* pol I, *Sulfolobus* sp. pol IVDNA polymerases.

In some embodiments, polymerase extension is not necessary. For example, the regions of the capture molecule complementary to the adaptor are adjacent to each other on the capture molecule. After annealing to the capture molecule, the ends of the adaptor can be directly ligated. In some embodiments, an asymmetric adaptor is used wherein the single-stranded regions of the adaptor are of unequal length. The regions of the capture molecule complementary to the asymmetric adaptor are adjacent to each other on the capture molecule. After annealing to the capture molecule, the longer and the shorter ends of the adaptor can be directly ligated.

In the next step, the extended 3'-end of the target nucleic acid strand is ligated to the 5'-end of the target nucleic acid strand creating a hybrid molecule containing the adaptor-ligated target nucleic acid strand a portion of which is annealed to the part of the ssdDNA molecule (FIG. 1). This hybrid molecule consists of two partially complementary single stranded circular molecules can be melted to separate the sscDNA molecule. In some embodiments, the melting is by heating. In other embodiments, the melting is chemical, e.g., by exposure to alkali or a similar nucleic acid duplex denaturing agent.

In some embodiments, the separated sscDNA molecule is removed by size separation or chromatography (beads, columns or gel electrophoresis). In embodiments where the sscDNA is biotinylated, it can be captured and removed by forming a biotin-streptavidin complex, e.g., with streptavidin-conjugated polymer coated magnetic or paramagnetic bead. In other embodiments, the sscDNA may be engineered to contain a nuclease digestion site. In some embodiments, the sscDNA is engineered to contain deoxyuracils. Such DNA can be removed by treatment with Uracil DNA N-glycosylase (UNG) and heating to convert the circular DNA into a linear form that can be digested with an exonuclease. In yet other embodiments, the sscDNA may be engineered to contain a photocleavable linker.

In some embodiments, the invention is a library of single-stranded circular molecules for nucleic acid sequencing wherein each circle comprises only one strand of the original target nucleic acid produced using the method of the invention. Each target nucleic acid in the library will contain the sequences of two adaptors and a portion of the sscDNA sequence.

In some embodiments, the invention is a method of sequencing nucleic acids via creation of a library of single-stranded circular nucleic acid molecules as described herein.

The present invention comprises generating a library of target nucleic acids from a sample for nucleic acid sequencing. Multiple nucleic acids, including all the nucleic acids in a sample may be converted into library molecules using the method and compositions described herein. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, or fecal samples). The sample may comprise whole blood or blood fractions where normal or tumor cells may be present. In some embodiments, the sample, especially a liquid sample may comprise cell-free material such as cell-free DNA or RNA including cell-free tumor DNA or tumor RNA or cell-free fetal DNA. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain nucleic acids derived from the cells in the culture or from an infectious agent present in the culture. In some embodiments, the infectious agent is a bacterium, a protozoan, a virus or a *mycoplasma*. The sample may also be an environmental sample containing or suspected to contain nucleic acids from organisms.

A target nucleic acid is the nucleic acid of interest that may be present in the sample. In some embodiments, the target nucleic acid is a gene or a gene fragment. In some embodiments, all the genes, gene fragments and intergenic regions (entire genome) constitute target nucleic acids. In some embodiments, only a portion of the genome, e.g., only coding regions of the genome (exome) constitute target nucleic acids. In some embodiments, the target nucleic acid contains a locus of a genetic variant, e.g., a polymorphism, including a single nucleotide polymorphism or variant (SNP of SNV), or a genetic rearrangement resulting e.g., in a gene fusion. In some embodiments, the target nucleic acid comprises a biomarker, i.e., a gene whose variants are associated with a disease or condition. In other embodiments, the target nucleic acid is characteristic of a particular organism and aids in identification of the organism or a characteristic of the pathogenic organism such as drug sensitivity or drug resistance. In yet other embodiments, the target nucleic acid is characteristic of a human subject, e.g., the HLA or KIR sequence defining the subject's unique HLA or KIR genotype.

In an embodiment of the invention, one or a plurality of target nucleic acids is converted into the template configuration of the invention. In some embodiments, the target nucleic acid occurs in nature in a single-stranded form (e.g., RNA, including mRNA, microRNA, viral RNA; or single-stranded viral DNA). In other embodiments, the target nucleic acid occurs in nature in a double-stranded form. One of skill in the art would recognize that the method of the invention has multiple embodiments. A single stranded target nucleic acid can be converted into double-stranded form and then subjected to the steps shown in FIG. 1. Longer target nucleic acids may be fragmented although in some applications longer target nucleic acids may be desired to achieve a longer read. In some embodiments, the target nucleic acid is naturally fragmented, e.g., circulating cell-free DNA (cfDNA) or chemically degraded DNA such as the one founds in chemically preserved or archived samples.

One of the advantages of the present invention is the ability to create single-stranded circular nucleic acids of unlimited length. The method of the invention does not have the low size limitations inherent in the single-stranded circle ligation (e.g., using CIRCLIGASE™, WO2010094040). The method also avoids the kinetic inefficiency of a splint ligation (See U.S. Application Pub. No. 20120003657).

The present invention utilizes adaptor molecules. In some embodiments, the adaptor is a double-stranded nucleic acid that at one end is capable of ligating the either end of the target nucleic acid. In some embodiments, the adaptor is phosphorylated at least one 5'-end. In some embodiments, the adaptor contains an overhang of one or more nucleotides to match the corresponding overhang created on the target nucleic acid.

In some embodiments, the adaptor comprises a double stranded region at one end and a single-stranded region at the other end. The double stranded region contains hybridized strands of nucleic acid while the single stranded region contains one strand or two strands not hybridized with each other. The end comprising the single stranded region is not capable of ligation to the target nucleic acid. In some embodiments, the adaptor is a Y-shaped adaptor (See Prashar and Weissman, (1996) Proc. Natl. Acad. Sci. USA 93:659). In some embodiments, the Y-adaptor is a symmetric Y-adaptor having single stranded regions that are the same or approximately the same length. In other embodiments, the adaptor is an asymmetric Y-adaptor having one single stranded region that is substantially longer than the other region.

In other embodiments, the adaptor has a stem-loop structure where the single stranded region is a linker connecting two strands of the double stranded region.

As described in further detail below, the double stranded end of the adaptor is ligated to each end of a double stranded target nucleic acid molecule. Ligation of double stranded nucleic acid molecules is well known in the art (See Green M., and Sambrook, J., *Molecular Cloning*, 2012 CSHL Press), and improvements on the general method are described herein. In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules or isolated non naturally-occurring molecules.

In some embodiments, the adaptor comprises one or more barcodes. A barcode can be a multiplex sample ID (MID) used to identify the source of the sample where samples are mixed (multiplexed). The barcode may also serve as a unique molecular ID (UID) used to identify each original molecule and its progeny. The barcode may also be a combination of a UID and an MID. In some embodiments, a single barcode is used as both UID and MID.

In some embodiments, each barcode comprises a predefined sequence. In other embodiments, the barcode comprises a random sequence. Barcodes can be 1-20 nucleotides long.

In some embodiments, the unique barcode (UID) is present in the double stranded portion of the adaptor. In these embodiments, each strand has a copy of the barcode (or the barcode complement) allowing for consensus sequencing and error correction as further described below and in U.S. App. Pub No. 20150044687.

In embodiments of the present invention, each target molecule is ligated to two adaptors. In some embodiments, each molecule has two unique barcodes (UID). In some embodiments, each molecule also carries the same multiplex sample ID (MID) barcode to identify the sample from which the target nucleic acid was derived.

In some embodiment, the invention comprises a pool of adaptors for creating a library of single stranded circular barcoded molecules. The adaptors within the pool have a unique barcode that are at least 1 or at least 3 edit distance apart from other barcodes in the pool. One of skill in the art would be able to determine what edit distance is optimal for a particular experiment based on typical error rates of a sequencing technology. Generally, greater edit distance means that fewer barcodes can be used in one pool. However, if the sequencing technology or a manufacturing process has a high error rate, greater edit distance will be required. For example, oligonucleotide manufacturing process used to make adaptors may have a high error rate. Similarly, a nucleic acid polymerase used in DNA amplification or primer extension in the sequencing-by-synthesis workflow can have a high error rate. These error rates would require increasing edit distance among the barcodes in adaptors of the pool. Conversely, improving the accuracy of each of the methods mentioned above will allow decreasing edit distance among the barcodes in adaptors of the pool.

In some embodiments, the invention comprises an article of manufacture represented by a single vial containing the entire pool of adaptors. Alternatively, an article of manufacture can comprise a kit where one or more adaptors of the pool are present in separate vials.

In some embodiments, the adaptor further comprises a primer binding site for at least one universal primer. A primer binding site is a sequence complementary to the primer to which primer can bind and facilitate strand elongation.

In some embodiments, the adaptor has more than one e.g., two primer binding sites. In some embodiments, one primer is used for amplification e.g., by PCR (including asymmetric PCR), linear amplification or rolling circle replication (RCA).

In some embodiments, the invention includes a step of preparing the target DNA for ligation of adaptors. In some embodiments, these steps include "polishing" e.g., converting molecules with strand overhangs into fully double stranded form by extending receded 3'-ends with a DNA polymerase or digesting protruding 3'-ends with a 3'-5' exonuclease such as Mung bean exonuclease.

In some embodiments, the double stranded ligation is a blunt-end ligation. In other embodiments, the double stranded ligation is a T-A ligation or other overhang ligation. In some embodiments, the method includes a step of adding a strand overhang to the target nucleic acid matching (i.e., complementary to) the overhang on the adaptor. In some embodiments, the overhang can be an added A nucleotide at one or both ends of the target nucleic acid while the adaptor is designed to contain a T nucleotide and the end to be ligated. The single nucleotide can be artificial synthesized during the in vitro synthesis of the adaptor molecule. The single nucleotide can also be enzymatically added e.g., by Taq polymerase or terminal transferase to one or both ends of the target nucleic acid. One or both.

The invention utilizes a single stranded circular capture DNA molecule (sscDNA). In some embodiments, the circular molecule is between 30 and 500 bases long. The molecule preferably consists of an artificial sequence or a modified naturally occurring sequence designed (or modified) to avoid self-complementarity within the circle and assure the single stranded conformation under the reaction conditions described herein.

The sscDNA molecule comprises at least two regions of complementarity with the adaptor sequences. The two regions of complementarity are positioned within the sscDNA molecule to ensure an energetically favorable topology of the hybrid molecule formed by the adaptor-ligated target DNA strand and the sscDNA molecule. In some embodiments, the two regions of complementarity with the adaptor sequences are spaced 1, 2, 5, 10 or more bases apart. In some embodiments, two regions of complementarity with the adaptor sequences are placed at a maximum distance from each other (diametrically opposite) in the circle.

In some embodiments, the sscDNA molecule contains additional artificial sequences not present in the adaptors. The sscDNA molecule may contain one or more primer binding sites, one or more barcodes, one or more restriction enzyme site or any other sequences needed to be incorporated into the target DNA molecule.

In some embodiments, an adaptor is not used. Instead, the capture molecule comprises target-specific regions to which a native target nucleic acid (not having exogenous sequences) can hybridize. In some embodiments, a limited library of target nucleic acids or a single species of target nucleic acid (e.g., the sequence of a pathogen, such as a viral pathogen e.g., HIV, or a bacterial pathogen, or a group of pathogens, e.g., *Streptococcus* sp.) can be detected. A limited library of capture molecules having a limited number of target-specific regions or a single species of capture molecules having two target-specific regions can be used.

In some embodiments, the capture molecules can be used to detect gene fusions. In such embodiments, the capture molecule has two target-specific regions, each capable of hybridizing to one of the fusion partners.

In some embodiments, the invention utilizes enzymes. The enzymes may include a DNA polymerase (including sequencing polymerase), a DNA ligase and a terminal transferase.

In some embodiments, the DNA polymerase is a non-strand displacing polymerase. In some embodiments, the polymerase may be selected from a Taq, Klenow, Bst, Pfu, T4, T7, *E. coli* pol I, *Sulfolobus* sp. pol IV DNA polymerases.

In some embodiments, the invention also utilizes a DNA ligase. In some embodiments, T4 DNA ligase or *E. coli* DNA ligase is used.

In some embodiments, the invention also utilizes a template-independent DNA polymerase, e.g., a terminal transferase or a DNA polymerase with the activity of adding one or more nucleotides in a template-independent manner. In some embodiments, the invention uses a mammalian terminal transferase or Taq polymerase.

The library of single-stranded circular barcoded molecules generated from the library can be subjected to nucleic acid sequencing. The template libraries created by the method of the present invention are especially advantageous in sequencing technologies adapted for sequencing circular templates of unlimited length or repeatedly reading a circular molecule, e.g., via rolling circle replication. Examples of such technologies include the Pacific BioSciences platform utilizing the SMRT® technology (Pacific Biosciences, Menlo Park, Calif.) or a platform utilizing nanopore technology such as those manufactured by Oxford Nanopore Technologies (Oxford, UK) or Roche Genia (Santa Clara, Calif.) and any other presently existing or future single-molecule sequencing technology that is suitable for sequencing circular templates of unlimited length or for repeatedly reading circular molecules. The sequencing step may utilize platform-specific sequencing primers. Binding sites for these primers may be introduced in adaptors used in the present invention. In some embodiments, binding sites for sequencing primers are introduced in the copied portion of the sscDNA. During the strand extension step connecting the 3'-end and the 5'-end of the target DNA molecule these primer binding sites will become incorporated into the target DNA molecules.

In some embodiments, the sequencing step involves sequence analysis. Sequence analysis may comprise secondary analysis, e.g., analysis performed on the sequence assembled by the instrument converting signals collected by the instrument into base calls (primary analysis). In some embodiments, the analysis includes a step of sequence aligning. In some embodiments, aligning is used to determine a consensus sequence from a plurality of sequences, e.g., a plurality having the same barcodes (UID). Such plurality of sequences with the same UID may be a product or amplification of the target nucleic acid molecule or of repeated reads of the circular nucleic acid molecules during sequencing, e.g., via rolling circle replication by a DNA polymerase or reading by the sequencing polymerase. In some embodiments, the barcodes (UIDs) are used to establish consensus sequences from the two strands of the target nucleic acid molecules. Although these strands become segregated into two separate single-stranded circular molecules, the two original strands carry the same UID from the adaptors (FIG. 1).

In other embodiments, generation of consensus sequences using barcodes (UIDs) comprises a step of eliminating artifacts, i.e., variations existing in some but not all sequences having an identical barcode (UID). Such artifacts can be eliminated from the consensus sequence because they likely result from amplification errors or sequencing errors.

In some embodiments, the copy number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

EXAMPLES

Example 1 (Prophetic) Creating a Library of Single-Stranded Barcoded Circular Molecules In this example, DNA is isolated from a patient's sample. In some instances, RNA is isolated from the sample and reverse-transcribed into cDNA that is treated in subsequent steps the same way as DNA isolated directly from the sample.

The DNA is end-repaired and A-tailed with T4 DNA polymerase. The addition of the A-tail allows for a subsequent efficient adaptor ligation, avoiding complications from blunt ligation. Next, a Y-shaped adaptor is ligated to both ends of the DNA using a T4 DNA ligase. The adaptor is pretreated with terminal transferase to add a T at each 3'-end. The adaptor is pretreated with T4 Poly nucleotide kinase to add a phosphate group to each 5'-end. The Y-shaped adaptor comprises a double stranded region that takes part in the ligation. The Y-shaped adaptor also comprises a single stranded region composed of two single strands that are not complementary and remain unhybridized. Following the ligation, the adaptor-ligated target molecules are heat-denatured and stored on ice.

A single stranded circular capture DNA molecule 30-500 bases in length is added to the sample. The capture molecules contain at least one biotinylated nucleotide. The capture molecules are attached to a surface of a magnetic bead decorated with streptavidin. The capture molecule contains two sequences, each complementary to each of the non-complementary strands in the adaptor. In the region between the two adaptor-complementary sequences the capture molecule contains a sample barcode and a primer binding site.

The capture molecule is added to the sample containing denatured the adaptor-ligated target molecules under conditions favoring specific DNA hybridization. The capture molecules are added in an optimal ratio and the Y-adaptor ends of the adaptor-ligated target molecules should attach with at least one end to them. Following the first hybridization, the other end of the target molecule is in spatial proximity to the adaptor-complementary sequence in the capture molecule and the likelihood of binding and second hybridization is high. The hybridization results in the formation of a hybrid molecule wherein the linear single stranded target nucleic acid is coupled to a capture molecule at its 3'- and 5'-ends.

The 3'-end of the target nucleic is extended in the presence of Pfu polymerase, dNTPs and magnesium at a suitable temperature. The polymerase is going around the circular capture molecule to reach the 5' end of the adaptor-ligated target nucleic acid that is bound to the capture molecule.

Next, T4 DNA ligase is added under conditions suitable for ligation. Ligation creates a hybrid molecule where a portion of the circular target molecule is hybridized to a portion of the circular capture molecule.

The hybrid molecule is captured and isolated from the sample using streptavidin decorated paramagnetic beads binding to the biotin-labeled capture molecule. The hybrid molecule is heat-denatured and the single stranded capture molecule is captured and removed again using streptavidin beads.

Once the creation of the library of circular target DNA molecules is completed, it can be used for circular consensus sequencing. Each circular molecule originating from one strand of the original DNA molecule is sequenced using SMRT® technology on the Pacific BioSciences instrument or using nanopore technology on a Genia instrument. The complementary strand will be sequenced in a different reaction.

The sequencing is following by bioinformatic analysis. The two strands are bioinformatically associated and consensus sequence is generated.

The invention claimed is:

1. A method of making a library of circular single-stranded target nucleic acid molecules from a sample comprising a plurality of double-stranded target nucleic acid molecules, the method comprising:
   (a) denaturing the double-stranded molecule, thereby forming two strands of the target molecule;
   (b) annealing a capture molecule to each strand of the target molecule, wherein the capture molecule is a circular single-stranded nucleic acid molecule comprising two sequences, wherein the two sequences comprise: (i) one sequence that is complementary to at least a portion of the 5'-end of the strand of the target molecule, and (ii) one sequence that is complementary to at least a portion of the 3'-end of the strand of the target molecule, thereby forming a hybrid molecule comprising the capture molecule hybridized to the sequences at the 5'-end and the 3'-end of the strand of the target molecule;
   (c) extending the 3'-end of the strand of the target molecule to reach the 5'-end of the strand of the target molecule;
   (d) ligating the 5'-end and the 3'-end of the strand of the target molecule, thereby forming a hybrid molecule comprising the capture molecule and a circularized strand of the target molecule; and
   (e) separating the capture molecule from the circularized strand of the target molecule, thereby forming a library of circular single-stranded target nucleic acid molecules.

2. The method of claim 1, wherein the capture molecule comprises a barcode.

3. The method of claim 1, wherein the capture molecule comprises a primer binding site.

4. The method of claim 1, wherein the capture molecule comprises a binding moiety for being captured by a solid support.

* * * * *